United States Patent [19]

Tanaka et al.

[11] Patent Number: 4,743,616
[45] Date of Patent: *May 10, 1988

[54] NOVEL BIOLOGICALLY ACTIVE COMPOUND HAVING ANTI-PROLYL ENDOPEPTIDASE ACTIVITY

[75] Inventors: Takaharu Tanaka; Naoki Higuchi; Masayuki Saitoh; Masaki Hashimoto, all of Osaka, Japan

[73] Assignee: Suntory Limited, Osaka, Japan

[*] Notice: The portion of the term of this patent subsequent to Oct. 20, 2004 has been disclaimed.

[21] Appl. No.: 760,411

[22] Filed: Jul. 30, 1985

[30] Foreign Application Priority Data

Jul. 31, 1984 [JP] Japan ................... 59-160994

[51] Int. Cl.⁴ ............... A61K 31/40; C07D 207/08
[52] U.S. Cl. ................... 514/423; 548/533; 548/540
[58] Field of Search ............ 548/533, 540; 514/423

[56] References Cited

U.S. PATENT DOCUMENTS

| | | | |
|---|---|---|---|
| 4,128,653 | 12/1978 | Cushman et al. | 514/315 |
| 4,154,937 | 5/1979 | Cushman et al. | 546/221 |
| 4,226,775 | 10/1980 | McEvoy et al. | 548/533 |
| 4,374,847 | 2/1983 | Gruenfeld | 514/415 |
| 4,439,611 | 3/1984 | Raghu et al. | 548/533 |
| 4,479,963 | 10/1984 | Gruenfeld | 548/430 X |

FOREIGN PATENT DOCUMENTS 0019411 11/1980 European Pat. Off. .

OTHER PUBLICATIONS

Noller, Chemistry of Organic Compounds, 3rd ed., (1965); pp. 150-151, 197; W. B. Saunders Co., Phila., Penna.

The Proceedings of the 1984 Annual Meeting of "The Agricultural Chemical Society of Japan", pp. 752-754.

Agri. Biol. Chem., 42 (12), pp. 2417-2419, 1978; Yoshimoto, et al.

L. Guoqiang et al, "Asymmetric Synthesis of 2-Alkylankanoic Acids Via Alkylation of Chiral Amide Anions", *Acta Chemica Scandinavica, Series B Organic Chemistry and Biochemistry*, vol. B38, No. 9, pp. 795-801, (1984).

L. Guoqiang et al, "Asymmetric Synthesis of 2-Alkylalkanoic Acids Via Alkylation of Chiral Amide Anions", *Chemical Abstracts*, vol. 101, (1984); 101:151374e.

D. J. Abraham et al., "Design, Synthesis, and Testing of Potential Antisickling Agents. 5 Disubstituted Benzoic Acids Designed for the Donor Site and Proline Salicylates Designed for the Acceptor Site", Journal of Medicinal Chemistry, vol. 27, No. 12 (1984) pp. 1549-1559.

F. R. Pfeiffer et al., "Tri- and Tetrrapeptide Analogues of Kinins as Potential Renal Vasodilators", Journal of Medicinal Chemistry, vol. 27, (1984) pp. 325-344.

Purushothaman et al, "The Structure of Roxburghilina, A Bis-Aminopyrrolidine from the Leaves of Aglaia Roxburghiana", *Journal of the Chemical Society Perkins Transactions 1*, pp. 3171-3174, (1979).

Primary Examiner—Joseph Paul Brust
Attorney, Agent, or Firm—Cushman, Darby & Cushman

[57] ABSTRACT

A novel compound that exhibits inhibitory activity against prolyl endopeptidase and a method for chemical synthesis of said compound, as well as its use as a prolyl endopeptidase inhibitor and an anti-amnesic agent that contains said compound as the active ingredient are provided.

9 Claims, No Drawings

NOVEL BIOLOGICALLY ACTIVE COMPOUND HAVING ANTI-PROLYL ENDOPEPTIDASE ACTIVITY

BACKGROUND OF THE INVENTION

The present invention relates to a novel compound that exhibits enzyme inhibiting activity against prolyl endopeptidase (EC, 3.4.21.26). The invention also relates to a method for chemical synthesis of such novel compound, as well as its use as a prolyl endopeptidase activity inhibitor and a drug, especially, an anti-amnesic agent, that contains it as the active ingredient.

Prolyl endopeptidase is known to inactivate neurotransmitters such as Substance P, thyrotropin-releasing hormone (TRH) and neurotensin, or vasopressin speculatively associated with memory. Tsuru and Yoshimoto of the Department of Pharmaceutical Sciences, Nagasaki University, found that compounds capable of inhibiting the prolyl endopeptidase activity were effective for preventing experimental amnesia caused in rats by scopolamine. Based on this discovery, they suggested the potential use of prolyl endopeptidase activity inhibitors as anti-amnesic agents (T. Yoshimoto and D. Tsuru, Agr. Biol. Chem. 42, 2417, 1978).

SUMMARY OF THE INVENTION

Motivated by the report of Tsuru and Yoshimoto, the present inventors made various efforts to find novel compounds that exhibited strong anti-amnesic activity and which yet had satisfactorily low toxicity levels. As a result, the inventors have found that N-acylpyrrolidine derivatives with anti-prolyl endopeptidase activity having the formula (I) shown below exhibited excellent effects against amnesia. The present invention has been accomplished on the basis of this finding.

DETAILED DESCRIPTION OF THE INVENTION

The N-acylpyrrolidine compounds of the present invention are represented by the formula (I):

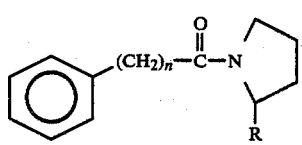

(wherein n is an integer of 1 to 4; R is a lower alkyl ester group, —$CH_2OH$ group or aldehyde group).

The compounds of formula (I) differ greatly from the known pyrasetam derivative based anti-amnesic agents in that the former contains a proline group. Because of this feature, the compounds of formula (I) present extremely low toxicity levels in organisms.

The following compounds of formula (I) are particularly preferred because of their high anti-prolyl endopeptidase activities:

Compound No. 1:

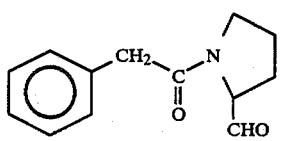

Compound No. 2:

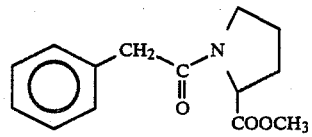

Compound No. 3:

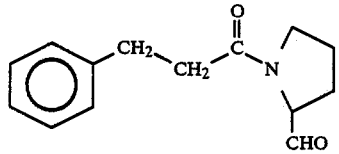

Compound No. 4:

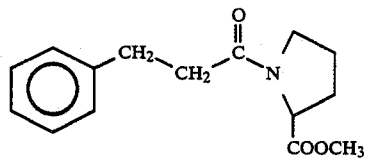

Compound No. 5:

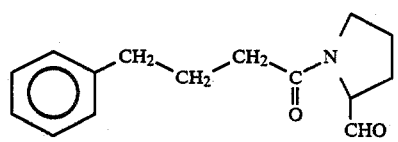

Compound No. 6:

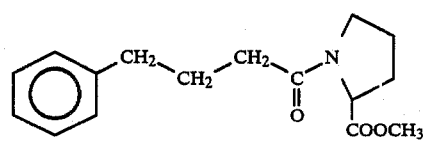

The compounds of formula (I) of the present invention may be synthesized by the following procedures:

(i) If the compounds have the formula (II) wherein R is a lower alkyl ester group in formula (I):

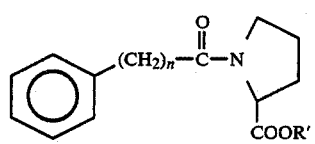

(wherein n is an integer of 1 to 4; R' is a lower alkyl group), they may be prepared from carboxylic acids of the formula:

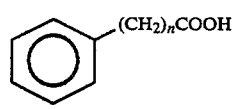

(wherein n is an integer of 1 to 4) and proline lower alkyl ester hydrochlorides by using any of the known methods used in peptide bond forming reactions, such as by the activated ester method (Synthesis 1).

Alternatively, the compounds of formula (II) may be readily synthesized from carboxylic acid chlorides of the formula:

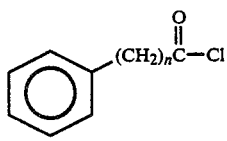

(wherein n is an integer of 1 to 4) and proline lower alkyl ester hydrochlorides by any of the conventional techniques (Synthesis 2).

(ii) If the end compounds have the formulas (III) and (IV) wherein R is —CH$_2$OH group or an aldehyde group, respectively, in formula (I):

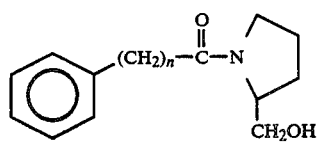 (III)

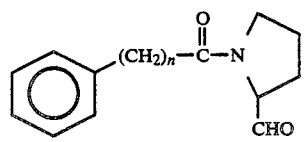 (IV)

(wherein n is an integer of 1 to 4), the following reactions may be used.

Methanol is added dropwise to a suspension of the compound of formula (II) and sodium borohydride in tertiary butyl alcohol, so as to produce an alcohol form (III) of the present invention. Besides tertiary butyl alcohol, tetrahydrofuran may be used as a solvent, and they are preferably used in the following volume ratios with respect to methanol:

tert-butyl alcohol: methanol = 5:1
tetrahydrofuran: methanol = 5:1.

The reaction is generally carried out at room temperature. The preferred temperature range is from room temperature to 100° C., with the range of 40°–70° C. being particularly preferred (Synthesis 3).

(iii) The compound of formula (III) may be further treated with a sulfur trioxide-pyridine complex to produce the compound of formula (IV). A suitable reaction solvent is dimethyl sulfoxide and the reaction may be carried at room temperature. A period not longer than 10 minutes will be sufficient. (Synthesis 4).

The desired compounds are obtained as oil.

The claimed compounds of the present invention were checked for their ability to inhibit the degestion of Z-glycyl-prolyl-β-naphthylamide by prolyl endopeptidase, and as will be shown in Example 8 given later in this specification, the tested compounds exhibited anti-prolyl endopeptidase activity. However, they showed not inhibitory effect at all against papain, bromelain, trypsin, chymotrypsin or thermolysin.

The compounds of the present invention prepared by the procedures described above are novel and, as will be apparent from the Examples, have anti-amnesic effects. The compounds may be used as anti-amnesic agents either independently or formulated together with known pharmaceutically acceptable excipients or carriers to provide suitable dosage forms such as capsules, tablets and injections. The compounds or anti-amnesic agents containing them as the active ingredient may be administered either orally or parenterally.

The compounds of the present invention are administered orally in 3 or 4 divided doses a day, each dose containing 2.5–250 mg of the active ingredient per adult. If the compounds are administered by intravenous dripping, the usual dose ranges from 0.05 to 5 mg/kg body weight. However, it is generally understood that the effective doses of anti-amnesic agents will vary depending upon the route of administration, the particular type of amnesia, the severity of the disease, and even upon the physical factors of the patient. Therefore, if such factors permit, the compounds of the invention may be administered in amounts outside the ranges specified above.

The present invention is hereunder described in greater detail by reference to Examples.

EXAMPLE 1

Synthesis of N-(3-phenylpropionyl)-proline methyl ester (Compound No. 4)

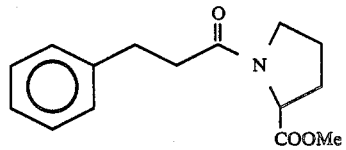

Proline methyl ester hydrochloride (3.4 g), 3-phenylpropionic acid (3.1 g) and triethylamine (2.8 ml) were suspended in dry methylene chloride (30 ml). To the cooled suspension, WSCD.HCl (N-ethyl-N',N'-dimethylaminopropylcarbodiimide hydrochloride) (3.9 g) was added. Under cooling, the mixture was stirred for 1 hour, and after allowing the mixture to warm to room temperature, it was again stirred for 12 hours. The stirred mixture was washed successively with water, 1N HCl, water, saturated aqueous sodium bicarbonate and brine. After drying over anhydrous magnesium sulfate, the solvent was distilled off under vacuum. The resulting crude product was purified by medium-pressure liquid column chromatography on silica gel (solvent: carbon tetrachloride) to obtain the end compound as an oil (4.6 g).

Instead of 3-phenylpropionic acid, a) 4-phenyl-n-butyric acid and b) 5-phenyl-n-valeric acid were used as starting compounds, and treated by the procedures described above to obtain the following end compounds as oil:

N—(4-phenyl-n-butyryl)-proline methyl ester (a')
(Compound No. 6)

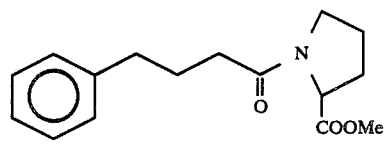

N—(5-phenyl-n-valeryl)-proline methyl ester (b')

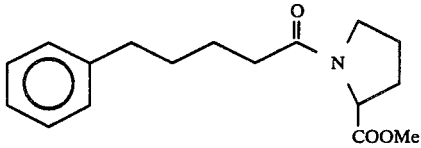

EXAMPLE 2

Synthesis of N-phenylacetyl-proline methyl ester (Compound No. 2)

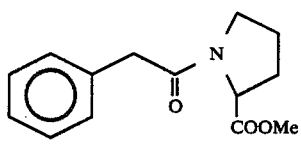

Proline methyl ester hydrochloride (3.3 g) and triethylamine (2.8 ml) were suspended in dry methylene chloride (30 ml). Under cooling, phenylacetylchloride (3.4 g) and triethylamine (3.1 ml) were simultaneously added dripwise to the suspension. Thereafter, the mixture was stirred at room temperature for 2 hours, and the reaction mixture was washed successively with water, 1N HCl, water, saturated aqueous sodium bicarbonate and brine. After drying over anhydrous magnesium sulfate, the solvent was distilled off under vacuum. The resulting crude product was purified by medium-pressure liquid column chromatography on silica gel (solvent: carbon tetrachloride) to obtain the end compound an an oil (3.7 g).

EXAMPLE 3

Synthesis of N-(3-phenylpropionyl)-prolinol

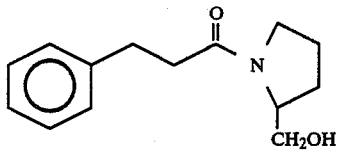

A mixture of N-(3-phenylpropionyl)-proline methyl ester (3.0 g) and sodium borohydride (1.1 g) was suspended in tertiary butyl alcohol (46 ml). To the stirred suspension, dry methanol (9.2 ml) was added dropwise under reflux. Thereafter, the mixture was stirred under reflux for 20 minutes. The heated mixture was cooled to room temperature and water (10 ml) was added under cooling with ice. Methanol and tertiary butyl alcohol were distilled off under vacuum and the residue was subjected to extraction with ethyl acetate. The extract was washed with brine and dried over anhydrous magnesium sulphate. The solvent was distilled off under vacuum and the resulting crude product was purified by medium-pressure ligand column chromatography on silica gel (solvent: chloroform) to obtain the end compound as an oil (2.7 g).

Instead of N-(3-phenylpropionyl)-proline methyl ester, (a) N-phenylacetyl-proline methyl ester (Compound No. 2), (b) N-(4-phenyl-n-butyryl)-proline methyl ester (Compound No. 6) and (c) N-(5-phenyl-n-valeryl)-proline methyl ester were used as starting compounds and treated by the procedures described above to obtain the following end compounds as oil:

N—phenylacetyl-prolinol    (a')

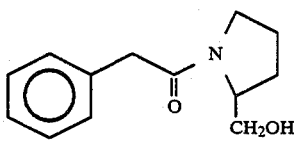

N—(4-phenyl-n-butyryl)-prolinol    (b')

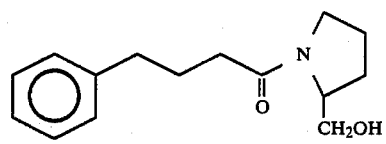

N—(5-phenyl-n-valeryl)-prolinol    (c')

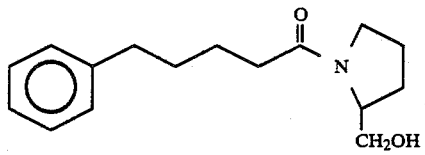

EXAMPLE 4

Synthesis of N-(3-phenylpropionyl)-prolinal (Compound No. 3)

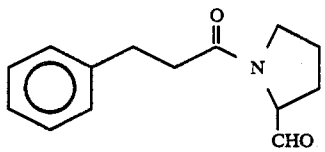

A mixture of N-(3-phenylpropionyl)-prolinol (1.0 g) and triethylamine (1.3 g) was dissolved in anhydrous dimethyl sulfoxide (14 ml), and to the stirred solution, a solution (13 ml) of sulfur trioxide-pyridine complex (2.1 g) in dimethyl sulfoxide was added. After stirring the mixture at room temperature for 10 minutes, the reaction solution was poured into iced water (150 ml) and subjected to extraction with ethyl acetate. The extract was washed successively with 10% aqueous citric acid, water, saturated aqueous sodium bicarbonate and brine, and dried over anhydrous magnesium sulfate. After distilling off the solvent under vacuum, the resulting crude product was purified by medium-pressure liquid column chromatography on silica gel (solvent: chloroform) to obtain the end compound as an oil (850 mg).

Instead of N-(3-phenylpropionyl)-prolinol, (a) N-phenylacetyl-prolinol, (b) N-(4-phenyl-n-butyryl)-prolinol and (c) N-(5-phenyl-n-valeryl)-prolinol were used as starting compounds and treated by the procedures described above so as to obtain the following end compounds as oil:

N—phenylacetyl-prolinal (Compound No. 1)    (a')

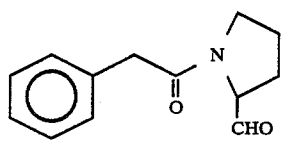

N—(4-phenyl-n-butyryl)-prolinal (Compound No. 5)    (b')

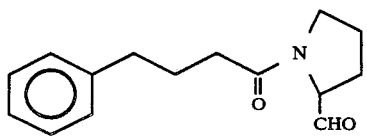

N—(5-phenyl-n-valeryl)-prolinal

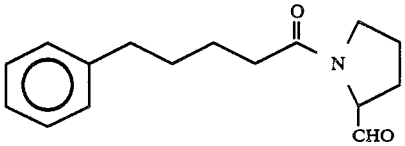 (c')

The analytical data for the compounds obtained in Examples 1 to 4 are listed in Table 1.

TABLE 1

| Compound | Molecular formula | $[\alpha]_D$ | IR($\nu_{max}^{neat}$) | H—NMR ($\delta$, CDCl$_3$) | MS (m/z) |
|---|---|---|---|---|---|
| (No. 2) phenylacetyl-proline methyl ester | C$_{14}$H$_{17}$NO$_3$ | $[\alpha]_D^{29}$ −73.1° (C = 1.32 CHCl$_3$) | 2960, 2880, 1740, 1650, 1420, 1200, 720, 700 | 1.68–2.20(4H,m), 3.60(3H,s), 3.30–3.80 (4H,m), 4.42(1H,m), 7.20(5H,s) | 247 (M$^+$) |
| (No. 4) 3-phenylpropanoyl-proline methyl ester | C$_{15}$H$_{19}$NO$_3$ | $[\alpha]_D^{29}$ −68.2° (C = 2.18 CHCl$_3$) | 3030, 2950, 2880, 1740, 1640, 1430, 1200, 750, 700 | 1.70–2.19(4H,m), 2.41–3.10(4H,m), 3,40(2H,m), 3.65(3H,s), 4.43(1H,m), 7.17(5H,s) | 261 (M$^+$) |
| (No. 6) 4-phenylbutanoyl-proline methyl ester | C$_{16}$H$_{21}$NO$_3$ | $[\alpha]_D^{29}$ −56.9° (C = 1.24 CHCl$_3$) | 2960, 2880, 1745, 1650, 1430, 1200, 750, 700 | 1.67–2.41(8H,m), 2.66(2H,m), 3.17–3.67 (2H,m), 3.64(3H,s), 4.43(1H,m), 7.14(5H,s) | 275 (M$^+$) |
| phenylacetyl-prolinol | C$_{13}$H$_{17}$NO$_2$ | $[\alpha]_D^{29}$ −51.4° (C = 2.24 CHCl$_3$) | 3390, 2950, 2880, 1620, 1430, 720, 700 | 1.60–1.95(4H,m), 3.23–3.62(6H,m), 4.10(1H,m), 4.92(1H,br), 7.20(5H,s) | 219 (M$^+$) |
| 3-phenylpropanoyl-prolinol | C$_{14}$H$_{19}$NO$_2$ | $[\alpha]_D^{26}$ −22.7° (C = 1.95 CHCl$_3$) | 3390, 2950, 2880, 1620, 1450, 750, 700 | 1.58–2.00(4H,m), 2.38–3.10(4H,m), 3.17–3.59(4H,m), 4.14(1H,m), 4.80(1H,br), 7.17(5H,s) | 233 (M$^+$) |
| 4-phenylbutanoyl-prolinol | C$_{15}$H$_{21}$NO$_2$ | $[\alpha]_D^{29}$ −14.9° (C = 1.53 CHCl$_3$) | 3390, 2950, 2880, 1620, 1450, 750, 700 | 1.58–2.39(8H,m), 2.64(2H,m), 3.18–3.64(4H,m), 4.08(1H,m), 4.91(1H,br), 7.16(5H,s) | 247 (M$^+$) |
| (No. 1) phenylacetyl-prolinal | C$_{13}$H$_{15}$NO$_2$ | $[\alpha]_D^{29}$ −109.5° (C = 1.07 CHCl$_3$) | 2980, 2885, 1730, 1635, 1420, 720, 700 | 1.60–2.24(4H,m), 3.40–3.72(4H,m), 4.44(1H,m), 7.32(5H,s), 9.49, 9.55(total 1H, both d, J=2Hz) | 217 (M$^+$) |

TABLE 1-continued

| Compound | Molecular formula | $[\alpha]_D$ | IR($\nu_{max}^{neat}$) | H—NMR ($\delta$, CDCl$_3$) | MS (m/z) |
|---|---|---|---|---|---|
| 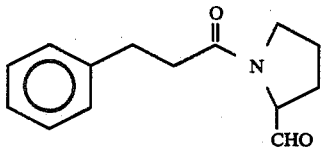 (No. 3) | C$_{14}$H$_{17}$NO$_2$ | $[\alpha]_D^{29}$ −50.6° (C = 1.03 CHCl$_3$) | 2970, 2880, 1730, 1630, 1430, 750, 700 | 1.60–2.20(4H,m), 2.54–3.05(4H,m), 3.26–3.65(2H,m), 4.38(1H,m), 7.23(5H,s), 9.49, 9.55(total 1H, both d, J=2Hz) | 231 (M$^+$) |
| 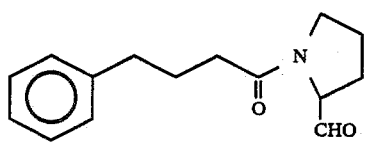 (No. 5) | C$_{15}$H$_{19}$NO$_2$ | $[\alpha]_D^{29}$ −33.7° (C = 1.13 CHCl$_3$) | 2950, 2880, 1730, 1640, 1430, 750, 700 | 1.70–2.43(8H,m), 2.70(2H,m), 3.30–3.68(2H,m), 4.44(1H,m), 7.24(5H,s), 9.50, 9.53(total 1H, both d, J=2Hz) | 245 (M$^+$) |

EXAMPLE 5

Synthesis of N-(6-phenyl-n-caproyl)-proline methyl ester

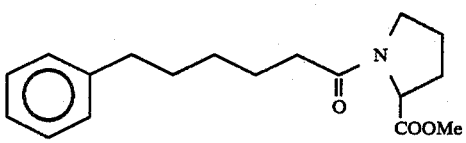

Proline methyl ester hydrochloride (2.4 g), 6-phenyl-n-caproic acid (2.8 g) and triethylamine (2.0 ml were suspended in dry methylene chloride (30 ml). To the cooled suspension, WSCD.HCl (N-ethyl-N',N'-dimethylaminopropyl carbodiimide hydrochloride) (2.7 g) was added. Under cooling, the mixture was stirred for 1 hour, and after allowing the mixture to warm to room temperature, it was again stirred for 12 hours. The stirred mixture was washed successively with water, 1N HCl, water, saturated aqueous sodium bicarbonate and brine. After drying over anhydrous magnesium sulfate, the solvent was distilled off under vacuum. The resulting crude product was purified by medium-pressure liquid column chromatography on silica gel (solvent system: CCl$_4$-chloroform) to obtain the end compound as an oil.

EXAMPLE 6

Synthesis of N-(6-phenyl-n-caproyl)-prolinol

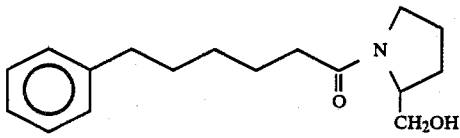

A mixture of N-(6-phenyl-n-caproyl)-proline methyl ester (2.5 g) and sodium borohydride (0.8 g) was suspended in tertiary butyl alcohol (34 ml). To the stirred suspension, dry methanol (6.8 ml) was added dropwise under reflux. Thereafter, the mixture was stirred under reflux for 20 minutes. The heated mixture was cooled to room temperature and water (10 ml) was added under cooling with ice. Methanol and tertiary butyl alcohol were distilled off under vacuum and the residue was subjected to extraction with ethyl acetate. The organic layer was washed successively with brine and dried over anhydrous magnesium sulfate. The solvent was distilled off under vacuum and the resulting crude product was purfied by medium-pressure liquid column chromatography on silica gel (solvent: chloroform) to obtain the end compound as an oil (2.1 g).

EXAMPLE 7

Synthesis of N-(6-phenyl-n-caproyl)-prolinal

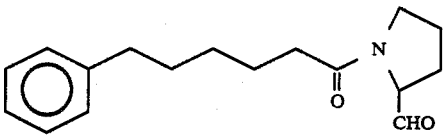

A mixture of N-(6-phenyl-n-caproyl)-prolinol (2.0 g) and triethylamine (2.2 g) was dissolved in anhydrous dimethyl sulfoxide (10 ml), and to the stirred solution, a solution (10 ml) of sulfur trioxide-pyridine complex (3.4 g) in dimethyl sulfoxide was added. After stirring the mixture at room temperature for 10 minutes, the reaction solution was poured into iced water (150 ml) and subjected to extraction with ethyl acetate. The organic layer was washed successively with 10% aqueous citric acid, water, saturated aqueous sodium bicarbonate and brine, and dried over anhydrous magnesium sulfate. After distilling off the solvent under vacuum, the resulting crude product was purified by medium-pressure liquid column chromatography on silica gel (solvent: chloroform) to obtain the end compound as an oil (0.7 g).

The analytical data for the compounds obtained in Examples 5 to 7 are listed in Table 2.

TABLE 2

| Compound | Molecular formula | $[\alpha]_D$ | IR $\nu$ max cm$^{-1}$ | H—NMR ($\delta$) | MS (m/z) |
|---|---|---|---|---|---|
| (Example 5) Ph-(CH₂)₄-CO-N(pyrrolidine-COOMe) | $C_{18}H_{25}NO_3$ | −57.35° (C = 0.68 CHCl₃) | (neat) 2920, 2800, 1740, 1640, 1420, 1190, 1160, 740, 700 | (CDCl₃) 1.49–2.70(14H,m), 3.44(2H,m), 3.65(3H,s), 4.43(1H,m), 7.13(5H,s) | 303 (M⁺) |
| (Example 6) Ph-(CH₂)₄-CO-N(pyrrolidine-CH₂OH) | $C_{17}H_{25}NO_2$ | −42.18° (C = 1.10 CHCl₃) | (neat) 3380, 2920, 2800, 1610, 1440, 740, 700 | (CDCl₃) 1.48–2.70(14H,m), 3.24–3.62(4H,m), 4.14(1H,m), 5.14(1H,t,J=5.4Hz), 7.14(5H,s) | 275 (M⁺) |
| (Example 7) Ph-(CH₂)₄-CO-N(pyrrolidine-CHO) | $C_{17}H_{23}NO_2$ | −99.08° (C = 0.98 CHCl₃) | (neat) 2920, 2850, 1720, 1630, 1420, 740, 700 | (CDCl₃) 1.34–2.08(10H,m), 2.27(2H,m), 2.59(2H,m), 3.46(2H,m), 4.34(1H,m), 7.14(5H,s), 9.42(1H,d,J=2Hz) | 273 (M⁺) |

EXAMPLE 8

Measurement of anti-prolyl endopeptidase activity

The method of Yoshimoto and Tsuru (T. Yoshimoto and D. Tsuru, Agr. Biol. Chem. 42, 2417, 1978) was used to measure the anti-prolyl endopeptidase activities of several compounds of the present invention. A mixture of 0.0025M Z-glycyl-proline-$\beta$-naphthylamide (0.25 ml), 0.1M phosphate buffer (pH, 7.0; 0.99 ml) and a solution of a particular anti-prolyl endopeptidase compound (0.01 ml) was incubated in a test tube at 37° C. for 3 minutes. Thereafter, 0.1 ml of a solution of prolyl endopeptidase (0.2 U/ml) was added and the mixture was heated at 35° C. for 10 minutes. After the reaction, 2.0 ml of Triton X-100 in 1M acetate buffer (pH, 4.0 ) was added to the reaction mixture until the final concentration of the surfactant was 10%. The mixture was left at room temperature for 15 minutes and the absorance (a) at 410 nm was measured.

A sample for blind test was prepared by using the buffer instead of the anti-prolyl endopeptidase compound and its absorbance (b) was also measured. The percent inhibition of prolyl endopeptidase was calculated by the formula: $((b-a)/b) \times 100$, and the amount of a specific compound to achieve 50% inhibition (IC$_{50}$) was determined. The results are shown in Table 3.

TABLE 3

| Compound No. | IC$_{50}$ ($\mu$g/test tube) |
|---|---|
| 1 | 0.8 |
| 2 | 200 |
| 3 | 0.018 |
| 4 | 60 |
| 5 | 0.006 |

TABLE 3-continued

| Compound No. | IC$_{50}$ ($\mu$g/test tube) |
|---|---|
| 6 | 25 |
| Sample prepared in Example 7 | 0.35 |

EXAMPLE 9

Measurement of preventive effect against experimental amnesia caused in rats by scopolamine (intraperitoneal administration)

Several of the anti-prolyl endopeptidase compounds of the present invention were checked for their ability to prevent the inhibition of long-term memory fixation by scopolamine. Solutions of physiological saline that contained selected compounds of the present inventions in varying amounts (20 mg, 2 mg, 0.2 mg and 0.02 mg/kg) were administered intraperitoneally once a day to Wister male rats (100–120 g). One hour after the administration, electric shocks were applied to the rats so that they would acquire passive avoidance learning. Immediately thereafter, scopolamine was administered intraperitoneally to each rat in an amount of 3 mg per kg of body weight.

The result of the test was assessed both 24 hours and 48 hours after the administration of scopolamine. The number of amnesic rats and that of sound rats were counted for each of the control group (rats which were not administered the test compounds but administered intraperitoneally only scopolamine and physiological saline) and the treated group (rats which were administered both the test compound and scopolamine). The results are shown in Tables 4 and 5.

TABLE 4

Amnesia test with rats (intrapritoneal administration)

| Sample | Drug administered after learning | No. of rats tested | Learning Initial avoidane time (sec.) | Learning No. of avoidances during learning | Learning learning time (sec.) | Pharmacological effects No. of amnesic rats/No. of rats tested | Pharmacological effects Percentage amnesia |
|---|---|---|---|---|---|---|---|
| physiological saline | physiological saline | 10 | 8.3 | 1.7 | 43.0 | 2/10 | 20[a] |
| physiological saline | scopolamine (3 mg/kg i.p.) | 10 | 2.9 | 1.9 | 46.2 | 9/10 | 90 |
| Compound No. 1 (0.2 mg/kg i.p.) | scopolamine (3 mg/kg i.p.) | 10 | 2.4 | 1.8 | 48.3 | 7/10 | 70 |
| Compound No. 1 (2 mg/kg i.p.) | scopolamine (3 mg/kg i.p.) | 10 | 3.5 | 1.8 | 45.2 | 3/10 | 30[a] |
| Compound No. 2 (20 mg/kg i.p.) | scopolamine (3 mg/kg i.p.) | 10 | 4.2 | 2.1 | 37.2 | 7/10 | 70 |
| Compound No. 3 (0.02 mg/kg i.p.) | scopolamine (3 mg/kg i.p.) | 15 | 2.4 | 1.6 | 41.0 | 7/15 | 47[d] |
| Compound No. 3 (0.2 mg/kg i.p.) | scopolamine (3 mg/kg i.p.) | 15 | 2.2 | 1.4 | 34.0 | 4/15 | 27[c] |
| Compound No. 3 (2.0 mg/kg i.p.) | scopolamine (3 mg/kg i.p.) | 10 | 3.1 | 2.3 | 43.2 | 4/15 | 27[c] |

[a] $p < 0.0001$
[b] $p < 0.001$
[c] $p < 0.01$
[d] $p < 0.05$

TABLE 5

Amnesia test with rats (intraperitonel administration)

| Sample | Drug administered after learning | No. of rats tested | Learning Initial avoidane time (sec.) | Learning No. of avoidances during learning | Learning learning time (sec.) | Pharmacological effects No. of amnesic rats/No. of rats tested | Pharmacological effects Percentage amnesia |
|---|---|---|---|---|---|---|---|
| physiological saline | physiological saline | 10 | 3.7 | 1.7 | 47.6 | 2/10 | 20[a] |
| physiological saline | scopolamine (3 mg/kg i.p.) | 10 | 3.5 | 1.5 | 40.1 | 10/10 | 100 |
| Compound No. 4 (2 mg/kg i.p.) | scopolamine (3 mg/kg i.p.) | 10 | 2.8 | 2.1 | 39.8 | 8/10 | 80 |
| Compound No. 4 (20 mg/kg i.p.) | scopolamine (3 mg/kg i.p.) | 10 | 2.9 | 1.6 | 40.5 | 4/10 | 40[d] |
| Compound No. 5 (0.02 mg/kg i.p.) | scopolamine (3 mg/kg i.p.) | 15 | 2.4 | 1.9 | 44.3 | 4/15 | 27[c] |
| Compound No. 5 (0.2 mg/kg i.p.) | scopolamine (3 mg/kg i.p.) | 15 | 2.1 | 1.8 | 42.9 | 2/15 | 13[b] |
| Compound No. 5 (2.0 mg/kg i.p.) | scopolamine (3 mg/kg i.p.) | 15 | 2.4 | 2.0 | 37.4 | 3/15 | 20[b] |
| Compound No. 6 (0.2 mg/kg i.p.) | scopolamine (3 mg/kg i.p.) | 10 | 2.7 | 1.4 | 43.5 | 5/10 | 50 |
| Compound No. 6 (2.0 mg/kg i.p.) | scopolamine (3 mg/kg i.p.) | 10 | 3.2 | 1.7 | 42.9 | 3/10 | 30[d] |

[a] $p < 0.0001$
[b] $p < 0.001$
[c] $p < 0.01$
[d] $p < 0.05$

EXAMPLE 10

Evaluation of preventive effect against experimental amnesia caused in rats by scopolamine (oral administration)

Compound No. 5 which proved particularly effective in preventing amnesia in Example 9 was further checked for its ability to prevent amnesia when it was administered orally.

Varying amounts (1, 5, 25 and 100 mg/kg) of the compound were administered orally to each of the rats and tested for its anti-amnesic effects by the same procedures as used in Example 9. The results are shown in Table 6, from which one can see that compound No. 5 exhibited the strongest anti-amnesic action when administered orally in an amount of 5 mg/kg.

TABLE 6

| | | | Learning | | | Pharmacological effects | |
|---|---|---|---|---|---|---|---|
| Sample | Drug administered after learning | No. of rats tested | Initial avoidance time (sec.) | No. of avoidances during learning | learning time (sec.) | No. of amnesic rats/No. of rats tested | Percentage amnesia |
| physiological saline | physiological saline | 10 | 2.8 | 1.6 | 49.2 | 1/10 | 10 |
| physiological saline | scopolamine (3 mg/kg i.p.) | 10 | 2.7 | 1.7 | 48.4 | 8/10 | 80 |
| Compound No. 5 (1 mg/kg p.o.) | scopolamine (3 mg/kg i.p.) | 10 | 2.3 | 1.9 | 45.3 | 4/10 | 40 |
| Compound No. 5 (5 mg/kg p.o.) | scopolamine (3 mg/kg i.p.) | 10 | 2.8 | 1.9 | 47.7 | 1/10 | 10 |
| Compound No. 5 (25 mg/kg p.o.) | scopolamine (3 mg/kg i.p.) | 10 | 2.1 | 1.3 | 39.1 | 3/10 | 30 |
| Compound No. 5 (100 mg/kg p.o.) | scopolamine (3 mg/kg i.p.) | 10 | 2.4 | 1.5 | 43.3 | 8/10 | 80 |

EXAMPLE 11

Acute toxicity test in mice

The compounds of the present invention were checked for their acute toxicity in CDF-1 strain male mice (body weight: 27.2–30.1 g) purchased from Awazu Laboratory Animals Co., Ltd.

Test samples were prepared by dissolving the respective compounds in DMSO, and mixing with an equal amount of physiological saline. A portion (0.1 ml) of the so conditioned test sample was administered intraperitoneally to each of the mice used. Each of the tested groups consisted of five mice. At 24 and 48 hours of the administration, the mice were observed. The average amount of each test compound administered in this Example is shown in Table 7.

TABLE 7

| Compound No. | Average dose (mg/kg) |
|---|---|
| 1 | 534.8 |
| 2 | 535.3 |
| 3 | 542.8 |
| 4 | 541.6 |
| 5 | 534.0 |
| 6 | 536.2 |

Each of the groups tested remained sound and showed no sign of intoxication at 24 or 48 hours of the administration of the doses shown in Table 7.

As will be understood from the foregoing description, the compounds of the present invention exhibit appreciable anti-prolyl endopeptidase activity and anti-amnesic effects. Acute toxicity test results show that the compounds caused no toxicity even when they were administered in such a high dose as about 500 mg/kg/mouse. Because of this relatively wide margin of safety as compared with their remarkable anti-prolyl endepeptidase activity, the compounds of the present invention hold promise as pharmaceuticals for preventing and curing amnesia.

What is claimed is:

1. An N-acylpyrrolidine derivative of formula (I):

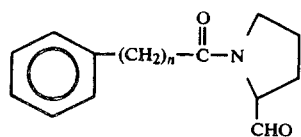

(I)

wherein n is a number of 1 to 4.

2. A pharmaceutical composition containing as the active ingredient a pharmaceutically effective amount of an N-acylpyrrolidine derivative of formula (I):

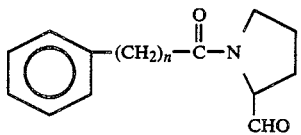

(I)

wherein n is a number of 1 to 4; together with a pharmaceutically acceptable excipient or carrier.

3. The pharmaceutical composition according to claim 2 wherein said pharmaceutically effective amount is an amount sufficient to exert an anti-amnesic effect.

4. A pharmaceutical composition containing as the active ingredient a pharmaceutically effective amount of a compound of formula:

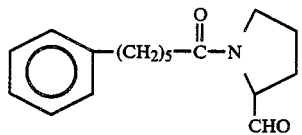

together with a pharmaceutically acceptable excipient or carrier.

5. A pharmaceutical composition according to claim 4 wherein said pharmaceutically effective amount is an amount sufficient to exert an anti-amnesic effect.

6. A compound of formula:

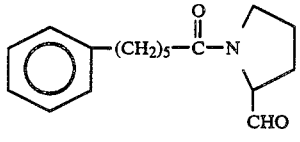

7. The N-acylpyrrolidine derivative according to claim 1, wherein n=1, N-phenylacetyl-prolinal.

8. The N-acylpyrrolidine derivative according to claim 1, wherein n=2, N-(3-phenylpropionyl)-prolinal.

9. The N-acylpyrrolidine derivative according to claim 2, wherein n=3, N-(4-phenyl-n-butyryl)-prolinal.

* * * * *